United States Patent [19]

Maekawa

[11] Patent Number: 4,905,655
[45] Date of Patent: Mar. 6, 1990

[54] FUEL INJECTOR ASSEMBLY WITH AN ALCOHOL SENSOR

[75] Inventor: Hiroko Maekawa, Himeji, Japan

[73] Assignee: Mitsubishi Denki Kabushiki Kaisha, Tokyo, Japan

[21] Appl. No.: 282,796

[22] Filed: Dec. 12, 1988

[30] Foreign Application Priority Data

Dec. 23, 1987 [JP] Japan .................... 62-195200[U]

[51] Int. Cl.$^4$ ................. F02B 75/12; F02D 41/04; G01F 1/56
[52] U.S. Cl. .................... 123/494; 123/1 A; 123/575; 73/116; 73/861.08
[58] Field of Search ............... 123/1 A, 478, 381, 491, 123/494, 575, 576, 577, 578; 73/116, 117.3, 861.08, 304 C; 324/453

[56] References Cited

U.S. PATENT DOCUMENTS

| | | | |
|---|---|---|---|
| 4,438,749 | 3/1984 | Schwippert | 123/381 X |
| 4,470,300 | 9/1984 | Kobayashi | 73/304 C |
| 4,480,484 | 11/1984 | Ueyama | 73/861.08 |
| 4,484,582 | 11/1984 | Rottenberg et al. | 73/861.08 |
| 4,568,874 | 2/1986 | Kramer et al. | 73/304 C X |
| 4,594,968 | 6/1986 | Degobert et al. | 123/494 X |
| 4,706,630 | 11/1987 | Wineland et al. | 123/494 X |
| 4,770,129 | 9/1988 | Miyata et al. | 123/494 X |

FOREIGN PATENT DOCUMENTS 183435 11/1986 Japan .

Primary Examiner—Willis R. Wolfe
Attorney, Agent, or Firm—Sughrue, Mion, Zinn, Macpeak and Seas

[57] ABSTRACT

A fuel injector assembly for an internal combustion engine of an automobile including an alcohol sensor is disclosed. The assembly comprises a hollow cylindrical fuel delivery pipe having nozzles formed on the circumferential side wall thereof. A pair of hollow cylindrical metallic plates having a plurality of radially extending throughholes are dispsed coaxially in the fuel delivery pipe to form a small gap therebetween, through which the fuel supplied from the fuel tank by a fuel bump flows before being injected from the valves of the nozzles into the intake manifold of the engine. The throughholes in the two metallic plates are axially displaced and some of the throughholes in the metallic plate of the larger diameter are axially and circumferentially aligned with the nozzles. The change of the capacitance of the capacitor formed by the pair of metallic plates and the fuel flowing therebetween is measured to determine the variation of the dielectric constant of the fuel. The alcohol content of the fuel mainly consisting of gasoline is computed from the dielectric constant thereof. Further, the amount of the fuel injected from the valves are controlled in accordance with the alcohol content.

5 Claims, 2 Drawing Sheets

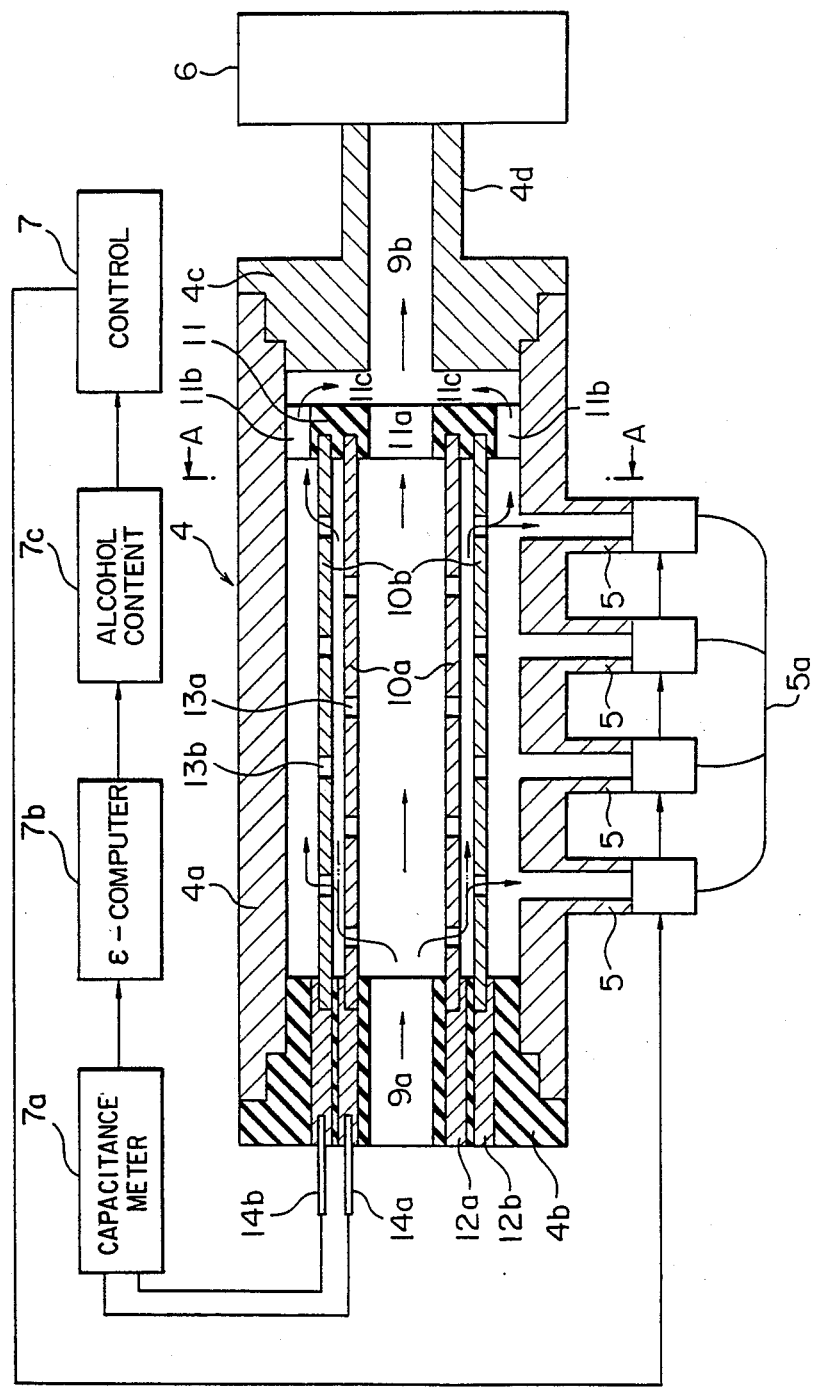

FUEL INJECTOR ASSEMBLY WITH AN ALCOHOL SENSOR

BACKGROUND OF THE INVENTION

1. Field of the Invention

The present invention relates to a fuel supply system of an internal combustion engine for automobiles, and more particularly to a fuel injector assembly including an alcohol sensor.

2. Description of the Prior Art

Gasolines are commonly used as the fuel for internal combustion engines for automobiles. The fuel is sprayed into an intake manifold and the mixture of air and fuel is supplied to the cylinders of the engine. The mixture is burned in the cylinders to convert the resulting heater into mechanical power by the pistons sliding in the cylinders. Thus, it is important to control the air to fuel ratio supplied to the cylinders at an optimum level best suited to the working conditions of the engine to ensure best performance thereof.

Gasolines used as fuels of internal combustion engines, however, are devided into various grades, and some of them include alcohols (methanol and/or ethanol) up to 15 percent. The inclusion of alcohols in gasolines substantially reduces the octane number of the fuel. Thus, if the air to fuel ratio is not modified according to the amount of alcohols added to the gasoline, the engine has the tendency to knock during starting. The tendency of knocking is especially manifest at the hot re-starting state of the engine.

Thus, Japanese laid-open utility model application No. No. 61-183435 proposes a fuel injector device for an internal combustion engine comprising a means for detecting the percentage of alcohols in the fuel. Utilizing the fact that the dielectric constant of alcohol is much greater than that of gasoline, the device of the Japanese utility model application determines the percentage of alcohol in the fuel by measuring the dielectric constant of the fuel. The device modifies the air to fuel ratio supplied to the engine in accordance with the detected percentage of alcohol in the fuel.

FIG. 1 shows a block diagram of a fuel injector device including an alcohol sensor. The device of FIG. 1 is similar to that disclosed in the above-mentioned Japanese utility model application. The fuel in the fuel tank 1 is pressurized by a fuel pump 2, and is supplied through a fuel pipe 2a to a fuel filter 3, and therefrom to a fuel delivery pipe 4 having nozzles 5. The fuel is injected from the valves of the nozzles 5 into an intake manifold coupled to the cylinders of the internal combustion engine. The pressure of the fuel is regulated by a fuel pressure regulator 6, and the fuel which is not injected into the manifold is returned through the fuel pipe 2a to the tank 1. The opening period of the valves of the nozzle 5 is controlled by the control unit 7 according to the measurements made by an alcohol sensor 8 disposed in the tank 1, so that the air to fuel ratio is adjusted to the optimum level.

The fuel injector of the above mentioned type, however, has the following two disadvantages:

The first disadvantage results from the delay between the time of measurement and that of injection. Namely, if the engine is started immediately after an amount of fuel is poured into the tank 1 in which a small amount of fuel remains which has an alcohol content different from that of the added fuel, then the fuel injected into the intake manifold immediately thereafter is that remaining in the fuel supply system between the tank 1 and the fuel delivery pipe 4, which fuel has an alcohol content different from that of the fuel in the tank 1. However, the sensor 8 detects the percentage of alcohol in the fuel in the tank 1. As the tubing from the tank 1 to the valves of nozzles 5 is relatively long, the air to fuel ratio is controlled to a wrong level, during an appreciable time period during which the old fuel in the fuel supply system is consumed, on the basis of the measurement of the alcohol content which is different from that of the fuel being injected. Thus, starting problems of the engine tend to occur.

The second disadvantage results from the position of the alcohol sensor in the tank 1. Namely, it is necessary to position the sensor 8 at the bottom of the tank 1 to ensure that the measurement of the alcohol content can be effected even when the fuel level lowers to be near to the bottom of the tank 1. In addition, water occasionally contained in the fuel tends to accumulate near the bottom portion of the tank. Thus, the measurement by the alcohol sensor situated at the bottom of the tank is adversely affected by the presence of this accumulating water which exhibits a very large dielectric constant. Consequently, the alcohol content of the fuel determined by the sensor tends to contain a large error due to the water which may be present in the tank. The air to fuel ratio may thus be controlled to a wrong level, and engine problems may ensue.

SUMMARY OF THE INVENTION

Thus, a main object of the present invention is to provide a fuel injector assembly for an internal combustion engine which is capable of adjusting the air to fuel ratio to an optimum level that is best suited to the alcohol content of the fuel being injected into the intake manifold of the engine, so that the best performance of the engine, especially at the starting period, is ensured.

A further object of the present invention is to provide a simple, economical, and accurate alcohol sensor structure of such a fuel injector assembly.

The fuel injector assembly for an internal combustion engine according to the present invention comprises a hollow cylindrical fuel delivery member having nozzles formed on the circumferential side wall thereof. Each nozzle has a valve from which the fuel supplied from the fuel tank (through a fuel pipe and the fuel filter by means of a fuel pump, etc.) is injected into the intake manifold of the engine. A capacitor comprising a pair of opposing metallic plates is disposed in the hollow cylindrical fuel delivery member in such a position that the fuel supplied from the tank and injected into the intake manifold from the valves flows between the gap formed between the opposing metallic plates. Thus, the capacitance of the capacitor varies with the change of the dielectric constant of the fuel being injected into the intake manifold. A capacitance measuring means (i.e. a capacitance meter circuit) measures the capacitance of the capacitor, from which the dielectric constant computing means computes the dielectric constant of the fuel flowing between the metallic plates of the capacitor at the present moment. Further, an alcohol content computing means computes the alcohol content of the fuel from the dielectric constant computed by the dielectric constant computing means (and from those of alcohol and gasoline, which are both known). Thus, a control means controls (by adjusting the opening periods of the valves) the amount of fuel injected into the manifold of the engine so that the air to fuel ratio is regulated to the optimum level which best suits the alcohol content of the fuel.

It is preferred that the capacitor of the alcohol sensor comprises a pair of hollow cylindrical metallic members disposed coaxially in the hollow cylindrical fuel delivery members. Further, these hollow cylindrical metallic members are preferred to have a plurality of radially extending through holes which are axially displaced on the two metallic members, so that the fuel supplied from the fuel tank into the fuel delivery member from an inlet end thereof flows within the metallic member of the smaller diameter, and then through the holes thereof, through a gap between the two metallic members, and through the holes of the metallic member of the larger diameter, and is injected into the intake manifold from the valves of the nozzles formed on the side wall of the fuel delivery member. This structure of the capacitor ensures that the measurement of the alcohol content is made of the fuel which is injected into the manifold immediately before the injection.

BRIEF DESCRIPTION OF THE DRAWINGS

The features of the present invention which are believed to be novel are set forth with particularity in the appended claims. The present invention itself, however, both as to its structure and operation, will become more clear in the following detailed description of the preferred embodiments, taken in conjunction with the accompanying drawings, in which:

FIG. 2 is an axial sectional view of a fuel delivery pipe of a fuel injector assembly including a capacitor (constituting an alcohol sensor head) according to the present invention.

In the drawings, like reference numerals represent like or corresponding portions or parts.

DETAILED DESCRIPTION OF THE PREFERRED EMBODIMENTS

Figure 3:
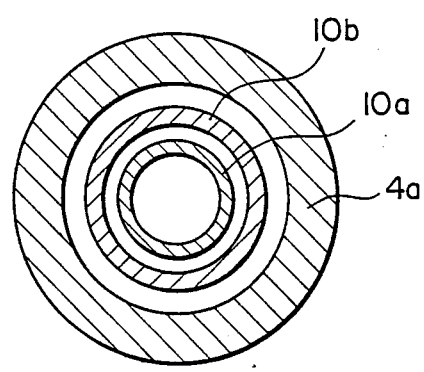
FIG. 3 shows a cross section of the fuel delivery pipe of FIG. 2 along the line A—A in FIG. 2.

Referring now to FIGS. 2 and 3 of the drawings, an embodiment according to the present invention will be described.

Figure 1:
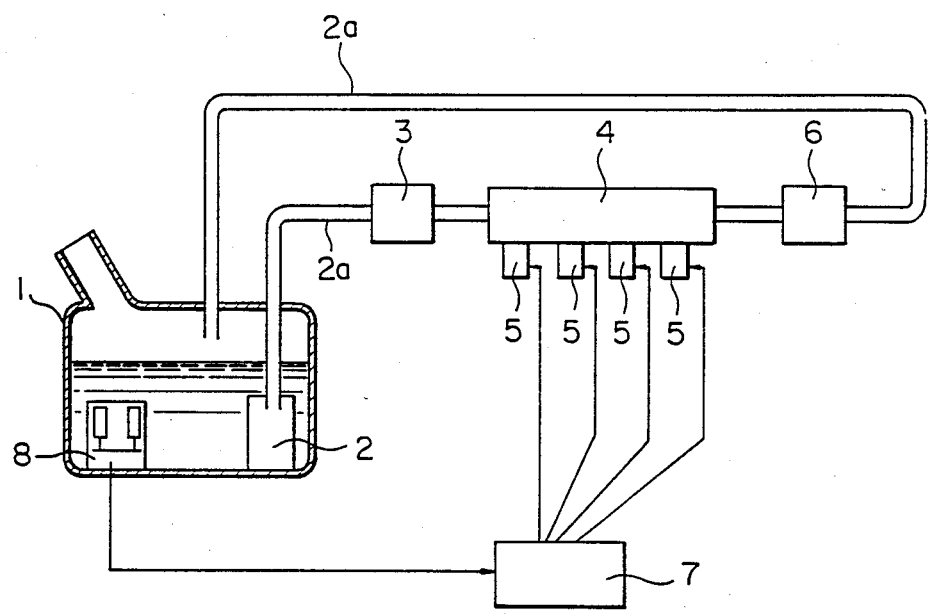
FIG. 1 shows, in diagrammatic form, a fuel supply system including an alcohol sensor, which is similar to the one proposed by a Japanese utility model application.

The fuel injector shown at FIG. 2 forms part of a fuel supply system which is similar to that shown at FIG. 1 except that the alcohol sensor (i.e. a capacitor) is not disposed in the fuel tank. Thus, the fuel (which consists mainly of gasoline, but may contain an appreciable amount of alcohol) is pressurized by a fuel pump in the fuel tank and is supplied through a fuel pipe and a fuel filter to the fuel delivery pipe 4 at the left end thereof in FIG. 2. Further, a fuel pressure regulator 6 coupled to the right end of the fuel delivery pipe 4 regulates the pressure of the fuel in the fuel delivery pipe 4. The fuel which is not injected from the valves of the fuel delivery pipe 4 is returned to the fuel tank through a fuel pipe connecting the fuel regulator 6 to the fuel tank.

The fuel delivery pipe 4 of FIG. 2 comprises a hollow cylindrical circumferential side wall 4a and a pair of disk-shaped end plates 4b and 4c having axially extending inlet and outlet ports 9a and 9b formed therethrough, respectively. The inlet port 9a is coupled to a fuel pump through a fuel pipe and a fuel filter (not shown), while the outlet port 9b is coupled to the fuel regulator 6 through an axially extending flange 4d of end plate 4c. The side wall 4a has a plurality of radially extending nozzles 5 each having a valve 5a for injecting the fuel into an intake manifold (not shown) coupled to the cylinders of the associated internal combustion engine (not shown) of an automobile.

A pair of hollow cylindrical metallic plate members 10a and 10b, which are coaxially disposed in the fuel delivery pipe 4 to form a small radial gap therebetween as shown in FIG. 3 in a radial cross section, are supplied at one end thereof by an electrically insulating member 11. The insulating member 11 has an axially extending central throughhole 11a, a plurality of peripheral throughholes 11b and two cylindrical grooves 11c formed through one side thereof for respectively supporting one end of the plate members 10a and 10b. The insulating member 11 is mounted to the side wall 4a near the end plate 4c to form an axial clearance 11c therebetween. The other ends of the hollow cylindrical metallic plate members 10a and 10b are coupled to and supported by annular electrically conducting layers 12a and 12b, respectively, which are coaxially embedded in the electrically insulating end plate 4b at the inlet side. The metallic members 10a and 10b each has a plurality of radially extending throughholes 13a and 13b, respectively, wherein the positions of the holes 13b in the larger diameter member 10b are axially displaced from those of the holes 13a in the smaller diameter member 10a. Further, some of the holes 13b in the larger diameter member 10b are axially and circumferentially in registry with the positions of the nozzles 5.

Thus, the fuel introduced into the fuel delivery pipe 4 from the inlet port 9a flows therethrough as shown by the arrows. First, the fuel flows into the interior of the smaller diameter hollow cylindrical metallic plate member 10a of and a portion thereof flows therethrough directly to the outlet port 9b. The remaining portion of the fuel flows through the holes 13a in the smaller diameter metallic plate member 10a, through the gap between the two metallic plate members 10a and 10b, and through the holes 13b in the larger diameter metallic plate member 10b. Thereafter, a portion of the fuel is injected from the valves 5a in the nozzles 5, while the remaining portion flows between the larger diameter metallic plate member 10b and the side wall 4a and through the holes 11b and the clearance 11c to the outlet port 9b.

The alcohol content of the fuel is determined utilizing the capacitor comprising the hollow cylindrical metallic plate members 10a and 10b and the fuel flowing therebetween, as will be described herebelow. A capacitance meter circuit 7a applies a voltage E (volts) across the two metallic plate members 10a and 10b through the electrodes 14a and 14b coupled to the electrically conducting layers 12a and 12b, and measures the capacitance C (farads) of the capacitor by means of the following equation:

$$Q = C \cdot E, \quad (1)$$

wherein Q is the electric charge (expressed in coulombs) on the plate members 10a and 10b. Further, a dielectric constant computing circuit 7b coupled to capacitance meter circuit 7a computes the dielectric constant $\epsilon$ (farads/meter) of the fuel flowing between the two metallic plate members 10a and 10b utilizing the following equation:

$$C = \epsilon \cdot S / d, \qquad (2)$$

wherein C is the capacitance expressed in farads (which has been determined by the capacitance meter circuit 7a by means of equation (1) above), S is the area (in square meters) of the opposing surface of either one of the two metallic plate members 10a and 10b, and d is the distance (in meters) between the opposing surfaces of the two metallic plate members 10a and 10b. Further, an alcohol content computing circuit 7c coupled to the dielectric constant computing circuit 7b computes the alcohol content k by volume from the value of the dielectric constant $\epsilon$ (farads/meter) obtained above, by solving the following equation:

$$\epsilon = (1-k) \cdot \epsilon 1 + k \cdot \epsilon 2, \qquad (3)$$

wherein $\epsilon 1$ and $\epsilon 2$ are the dielectric constants (expressed in farads per meter) of gasoline and alcohol, respectively, the values of which are both well known.

The control unit 7 controls the length of opening periods of the valves 5a of the fuel delivery pipe 4 during each cycle of the engine in accordance with the alcohol content k computed by the alcohol content computing circuit 7c, so that the amount of fuel injected into the manifold of the engine is regulated to adjust the air to fuel ratio to an optimum level best suited to the alcohol content k of the fuel. As is well known by those skilled in the art, the control unit 7 adjusts the length of the opening periods of the valves 5a not only in accordance with the alcohol content k but also in accordance with other working conditions of the engine.

The structure and position of the capacitor portion of the alcohol sensor according to the present invention ensures that the alcohol content of the fuel is measured immediately before being injected into the manifold. Thus, the speed of response is considerably enhanced. Further, the large area of the opposing metallic plate members of the capacitor ensures that the average alcohol content of the fuel which is injected into the manifold is measured. Thus, the accuracy of the measurement is also enhanced.

While description has been made of a particular embodiment of the present invention, it will be understood that many modifications may be made without departing from the spirit thereof. For example, the capacitor may comprise a pair of opposing pairs of coaxially disposed hollow cylindrical metallic plates, provided that the fuel injected into the manifold flows through the gap formed between the opposing pair of the metallic plates. The appended claims are contemplated to cover any such modifications as fall within the true spirit and scope of the present invention.

What is claimed is:

1. A fuel injector assembly for injecting a fuel supplied from a fuel tank into an intake manifold of an internal combustion engine, comprising:

a hollow cylindrical fuel delivery member having formed on a circumferential side wall thereof nozzles each having a valve adapted to inject the fuel supplied from said fuel tank into said intake manifold of the internal combustion engine;

a pair of opposing metallic plates disposed in said hollow cylindrical fuel delivery member along a path of flow of the fuel supplied from said fuel to said valves, thereby guiding the flow of the fuel in such a way that the fuel flows through a gap formed between said pair of opposing metallic plates;

capacitance measuring means electrically coupled to said pair of opposing metallic plates for measuring a capacitance of a capacitor formed by said pair of opposing metallic plates and the fuel flowing therebetween;

dielectric constant computing means, coupled to said capacitance measuring means, for computing a dielectric constant of the fuel flowing between said opposing metallic plates, from the capacitance measured by said capacitance measuring means;

alcohol content computing means, coupled to said dielectric constant computing means, for computing an alcohol content of the fuel from the dielectric constant computed by said dielectric constant computing means; and control means, coupled to said alcohol content computing means, for controlling an amount of fuel injected into said intake manifold in accordance with the alcohol content computed by said alcohol content computing means.

2. A fuel injector assembly as claimed in claim 1, wherein said pair of opposing metallic plates comprises a pair of hollow cylindrical metallic members of different diameters disposed coaxially in said hollow cylindrical fuel delivery member.

3. A fuel injector assembly as claimed in claim 2, wherein said pair of hollow cylindrical metallic members have a plurality of radially extending through holes.

4. A fuel injector assembly as claimed in claim 3, wherein the throughholes formed in the hollow cylindrical metallic member of a larger diameter are axially displaced with respect to the axial positions of the throughholes formed in the hollow cylindrical metallic member of a smaller diameter, thereby guiding the flow of said fuel supplied from the fuel tank into said hollow cylindrical fuel delivery member from an inlet end thereof, in such a way the the fuel flows first within the smaller diameter hollow cylindrical metallic member, and then through the throughholes in the smaller diameter hollow cylindrical metallic member, through a gap formed between the pair of hollow cylindrical metallic members, and through the through holes in the larger diameter hollow cylindrical metallic member, and is injected thereafter into the intake manifold from the valves of said nozzles formed on the side wall of the hollow cylindrical fuel delivery member.

5. A fuel injector assembly as claimed in claim 4, wherein at least a number of the throughholes formed in the larger diameter hollow cylindrical metallic member are positioned axially and circumferentially in registry with the axial and circumferential positions of said nozzles formed on the side walls of said hollow cylindrical fuel delivery member.

* * * * *